(12) United States Patent
Averick et al.

(10) Patent No.: US 11,999,848 B2
(45) Date of Patent: Jun. 4, 2024

(54) HYDROPHILIC POLYARYLENE ETHER KETONE POLYMER AND METHODS OF FORMING SAME

(71) Applicant: Allegheny Singer Research Institute, Pittsburgh, PA (US)

(72) Inventors: Saadyah Averick, Pittsburgh, PA (US); Boyle Cheng, Mars, PA (US); Andrew Kassick, Wexford, PA (US); Michael Oh, Irvine, PA (US)

(73) Assignee: Allegheny Singer Research Institute, Pittsburgh, PA (US)

( * ) Notice: Subject to any disclaimer, the term of this patent is extended or adjusted under 35 U.S.C. 154(b) by 886 days.

(21) Appl. No.: 16/967,456

(22) PCT Filed: Feb. 5, 2019

(86) PCT No.: PCT/US2019/016588
§ 371 (c)(1),
(2) Date: Aug. 5, 2020

(87) PCT Pub. No.: WO2019/156949
PCT Pub. Date: Aug. 15, 2019

(65) Prior Publication Data
US 2021/0222003 A1 Jul. 22, 2021

Related U.S. Application Data

(60) Provisional application No. 62/626,822, filed on Feb. 6, 2018.

(51) Int. Cl.
*C08L 71/12* (2006.01)
*A61L 27/18* (2006.01)
*C08G 65/48* (2006.01)
*C08K 5/17* (2006.01)

(52) U.S. Cl.
CPC .............. *C08L 71/12* (2013.01); *A61L 27/18* (2013.01); *C08G 65/485* (2013.01); *C08K 5/17* (2013.01); *C08G 2650/40* (2013.01); *C08L 2203/02* (2013.01)

(58) Field of Classification Search
None
See application file for complete search history.

(56) References Cited

U.S. PATENT DOCUMENTS

2006/0094852 A1  5/2006  Yuan et al.
2007/0256969 A1  11/2007  Ding et al.
2008/0020127 A1  1/2008  Whiteford et al.

FOREIGN PATENT DOCUMENTS

AU    2009228114 A1 * 10/2009
CA       2224780 A1 * 12/1997
WO  WO 2017/042159 A1 *  3/2017

* cited by examiner

*Primary Examiner* — Tae H Yoon
(74) *Attorney, Agent, or Firm* — Fox Rothschild LLP

(57) ABSTRACT

This patent document discloses a modified polymer having increased hydrophilicity and a method of preparing the same. A polyarylene ether ketone polymer having a plurality of repeating units, wherein one or more units of the plurality of repeating units contains a hydrophilic N-substituted imine, which is derived from a ketone in the one or more units.

41 Claims, No Drawings

HYDROPHILIC POLYARYLENE ETHER KETONE POLYMER AND METHODS OF FORMING SAME

RELATED APPLICATIONS AND CLAIM OF PRIORITY

This application is a national stage application of, and claims priority to International Patent Application No. PCT/US2019/16588, filed Feb. 5, 2019, which claims priority to U.S. Provisional Patent Application No. 62/626,822, filed Feb. 6, 2018, the disclosure of which are fully incorporated into this document by reference.

BACKGROUND

This patent document discloses a hydrophilic polyarylene ether ketone polymer and a method of efficient synthesis of the hydrophilic polymer. The new polymer finds applications in various medical fields including for example spinal interbody cages for arthrodesis or replacement of bone flaps in craniotomies Spinal interbody fusion is an important treatment procedure for pathologies afflicting the spine including degenerative disc disease contributing to low back pain. The process involves removal of a damaged vertebral disk and implantation of a fixative device that promotes spinal fusion via osseointegration of new bone tissue into the device. Commonly implanted fusion devices are titanium, poly(ether ether ketone) (PEEK) or a combination of the two (i.e., titanium coatings onto PEEK). These materials may be implanted with allograft bone to promote bone fusion. The primary advantage of a titanium based implant is rapid fusion and osseointegration. However, titanium based devices are radio-opaque and very hard, which can lead to challenges in imaging the implant site and the potential for damage to bone tissue. PEEK's modulus or stiffness more closely matches (compared to metals such as titanium) that of bone and does not adversely affect imaging studies, thus overcoming the primary drawbacks of titanium. But PEEK is not as conducive to osteoblast growth, leading to longer time lines for spinal fusion and thus greater risks of device failure. An ideal implant would promote osseointegration while matching (or being greater than) the hardness of bone and exhibit radiotransparency.

PEEK's poor osseointegrative properties are derived from its intrinsic hydrophobicity (water contact angle ~85-90). There are two established mechanisms for increasing PEEK's osseointegration properties and both require extensive surface modification of PEEK, either by etching pores and channels into PEEK to give more space for bone cells to seed or by coating the surface of PEEK with a layer of metal such as titanium or inorganic minerals. The drawbacks to current methods to improving PEEK osseointegration are that structural modification of PEEK's surface does not improve this polymer's hydrophilicity; spray coatings can delaminate and cause catastrophic device failure; and coating all surfaces of complex medical devices can lead to low throughput due to complex device geometries.

Thus, a need exists for improved hydrophilic polymers and a production procedure that is facile, economical and scalable.

SUMMARY

Described herein are novel hydrophilic polymers that are fabricated with a simple procedure involving benign conditions that are amenable to large scale production in various applications.

An aspect of this patent document discloses a polyarylene ether ketone polymer having a plurality of repeating units, wherein one or more units of the plurality of repeating units contains a hydrophilic N-substituted imine, which is derived from a ketone in the one or more units. In some embodiments, the N-substituted imine is not part of a N-hydroxy imine. In some embodiments, the units containing the ketone-derived hydrophilic group account for about 0.1% to about 25% of the plurality of repeating units. In some embodiments, the units containing the ketone-derived hydrophilic group account for about 0.1% to about 10% of the plurality of repeating units.

In some embodiments, the units containing the ketone-derived hydrophilic group are each independently represented by Formula I,

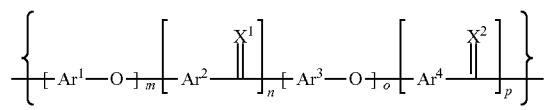

Formula I wherein:
Ar$^1$, Ar$^2$, Ar$^3$, and Ar$^4$ are each an optionally substituted aryl;
each of X$^1$ and X$^2$ is independently selected from O,

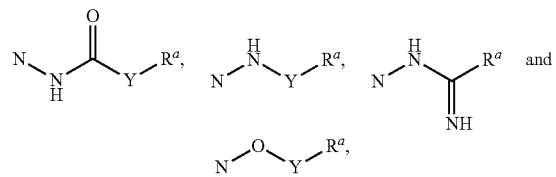

wherein:
Y is a C1-C10 alkylene, wherein one or more carbons in the C1-C10 alkylene is optionally replaced with a heteroatom, a carbonyl or NR$^1$R$^2$,
R$^a$ is selected from the group consisting of OR$^1$, NR$^1$R$^2$, C1-C5 alkyl, a primary, secondary, tertiary, or quaternary ammonium salt moiety, a pyridinium salt moiety, a guanidino or guanidinium salt moiety, a peptide, an amino acid, and zwitterionic species, wherein R$^1$ and R$^2$ are independently an H or a C1-C5 alkyl, and
provided that at least one of all the X$^1$s and all the X$^2$s in each of the one or more units is not O;
m and n are each an integer of 1, 2, or 3; and
and p are each an integer of 0, 1, or 2.

In some embodiments, o and p are each 0. In some embodiments, m is 1, n is 1, and o and p are each 0. In some embodiments, m is 1, n is 1, o is 0, and p is 1.

In some embodiments, only one of all the X$^1$s and all the X$^2$s in each of the one or more units is

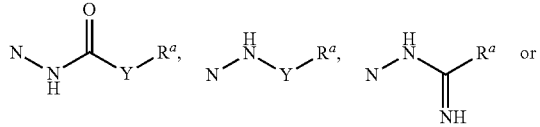

-continued

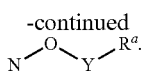

In some embodiments, $R^a$ is selected from the group consisting of $OR^1$, $NR^1R^2$, and a quaternary ammonium moiety. In some embodiments, $Ar^1$, $Ar^2$, $Ar^3$, and $Ar^4$ are each a phenyl group.

One aspect of this document discloses a medical device containing the polyarylene ether ketone polymer described herein as a surface coating component. In some embodiments, the device is an orthopedic implant. In some embodiments, the orthopedic implant is a vertebral disk implant.

Another aspect of this document discloses a method of promoting spinal fusion, comprising implanting in a subject in need the medical device described herein.

Another aspect of this document discloses a method of modifying a medical device comprising a surface polymer comprising a plurality of repeating units, whereby a ketone group of one or more units of the plurality of repeating units is converted to a hydrophilic derivative group, comprising
  (a) contacting the surface polymer with an agent selected from the group consisting of

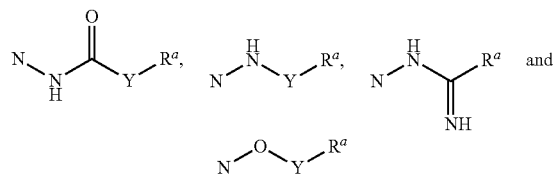

in a reaction medium
wherein:
  Y is a C1-C10 alkylene, wherein one or more carbons in the C1-C10 alkylene is optionally replaced with a heteroatom or a carbonyl; and
  $R^a$ is selected from the group consisting of $OR^1$, $NR^1R^2$, C1-C5 alkyl, a primary, secondary, tertiary, or quaternary ammonium moiety, a pyridinium salt moiety, a guanidino or guanidinium salt moiety, a peptide, an amino acid, or a zwitterionic species, wherein $R^1$ and $R^2$ are each an H or a C1-C5 alkyl; and
  (b) allowing the ketone functional group of the one or more units to react with the agent;
  wherein the one or more units having the hydrophilic group are independently represented by Formula I as described above.

In some embodiments, the method increases the hydrophilicity of the medical device. In some embodiments, the molar ratio between the surface polymer and the agent ranges from about 10:1 to about 1:100. In some embodiments, the reaction medium has a pH ranging from about 6.8 to about 8. In some embodiments, the reaction medium has a pH about 7.4. In some embodiments, the reaction medium comprises an acid, and the acid and the surface polymer are in a molar ratio ranging from about 100:1 to about 1:100. In some embodiments, the agent is in a form of an acid salt. In some embodiments, the agent is in a concentration ranging from about 0.1 mg/ml to about 1000 mg/ml. In some embodiments, the agent is in a concentration ranging from about 0.1 mg/ml to about 50 mg/ml. In some embodiments, the surface polymer is submerged in the reaction medium. In some embodiments, the reaction medium comprises a polar solvent. In some embodiments, step (b) takes place at a temperature of less than about 65° C. In some embodiments, the medical device is an implant.

DETAILED DESCRIPTION

This document discloses a medical device containing a modified surface polymer, as well as features of such a polymer and methods of making such a polymer. Depending on the specific groups introduced to the polymer, the modification imparts desirable properties to the medical device. In particular, a surfaced modified implant having improved hydrophilicity promotes bone fusion via osseointegration of new bone tissue into the device. In comparison with conventional polymers, the modified surface polymers disclosed in this document are more conducive to osteoblast growth. In addition, the modification of the polymer described herein allows for the introduction of various functional groups and can be accomplished efficiently. Further, the ease of adaptability may allow the new polymers to be used for various other applications.

While the following text may reference or exemplify specific embodiments of a modified polymer or a method of modifying the polymer, it is not intended to limit the scope of the invention to such particular reference or examples. Various modifications may be made by those skilled in the art, in view of practical and economic considerations, such as the amount of the hydrophilic group in the polymeric units and its ratio relative to the overall units of the polymer.

The articles "a" and "an" as used herein refers to "one or more" or "at least one," unless otherwise indicated. That is, reference to any element or component of the present invention by the indefinite article "a" or "an" does not exclude the possibility that more than one element or component is present.

The term "about" as used herein refers to the referenced numeric indication plus or minus 10% of that referenced numeric indication.

The term "alkyl" refers to monovalent or divalent saturated alkane radical groups particularly having up to about 18 carbon atoms, more particularly as a lower alkyl, from 1 to 8 carbon atoms and still more particularly, from 1 to 6 carbon atoms. The hydrocarbon chain may be either straight-chained or branched. The term "C1-C10 alkyl" refers to alkyl groups having 1, 2, 3, 4, 5, 6, 7, 8, 9 or 10 carbon atoms. Similarly, the term "C1-C4 alkyl" refers to alkyl groups having 1, 2, 3, or 4 carbon atoms. Non-limiting examples of alkyls include (a) and monovalent groups such as methyl, ethyl, n-propyl, isopropyl, n-butyl, iso-butyl, tert-butyl, n-hexyl, n-octyl, and tert-octyl; and (b) divalent groups such as —CH2- (methylene), —CH2CH2-, and —CH2CH2CH2-.

An aspect of the document provides a polyarylene ether ketone polymer having a plurality of repeating units, wherein one or more units of the plurality of repeating units contains a hydrophilic N-substituted imine derivative group, which is derived from a ketone in the one or more units.

The polyarylene ether ketone polymer is generally prepared via reaction of an aromatic dihalogen compound with a bisphenol and/or of a halophenol in the presence of alkali metal carbonate or alkaline earth metal carbonate or alkali metal hydrogen carbonate or alkaline earth metal hydrogen carbonate in a high-boiling aprotic solvent to give a desired product. Non limiting examples of polyarylene ether ketone polymers include polyether ether ketone (PEEK), polyether ketone (PEK), polyether ketone ketone (PEKK), or a polyether ether ketone ketone (PEEKK). Other arrangements of the carbonyl groups and oxygen groups are, of course, also possible.

Depending on the reaction condition and the target application, the polyarylene ether ketone polymer can have from about 0.1% to about 25% of its repeating units modified to contain a hydrophilic group. In some embodiments, the modified units account for about 0.1% to about 15%, about 0.1% to about 10%, about 0.1% to about 5%, or about 0.1% to about 2% of the original repeating units.

Each of the modified units containing the hydrophilic derivative group derived from the ketone group are independently represented by Formula I,

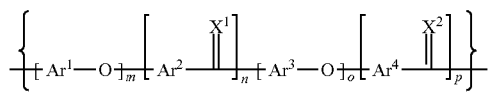

Formula I

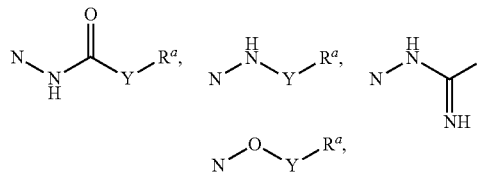

wherein:
Ar$^1$, Ar$^2$, Ar$^3$, and Ar$^4$ are each an optionally substituted aryl;
each of X$^1$ and X$^2$ is independently selected from O,

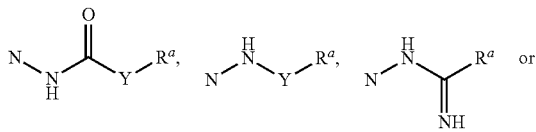

wherein:
Y is a C1-C10 alkylene, wherein one or more carbons in the C1-C10 alkylene is optionally replaced with a heteroatom, a carbonyl or NR$^1$R$^2$,
R$^a$ is selected from the group consisting of OR$^1$, NR$^1$R$^2$, C1-C5 alkyl, a primary, secondary, tertiary, or quaternary ammonium salt moiety, a pyridinium salt moiety, a guanidino or guanidinium salt moiety, a peptide, an amino acid, or a zwitterionic species, wherein R$^1$ and R$^2$ are independently an H or a C1-C5 alkyl, and
provided that at least one of all the X$^1$s and all the X$^2$s in each of the one or more units is not O;
m and n are each an integer of 1, 2, or 3; and
and p are each an integer of 0, 1, or 2.

The modified units can be the same or different from each other. For example, a copolymer of PEEK and PEKK, after the ketones in their respective repeating units are modified, will have different modified units from PEEK and PEKK.

In some embodiments, o and p are each 0. In some embodiments, m is 1, n is 1, and o and p are each 0. In some embodiments, m is 1, n is 1, o is 0, and p is 1.

In some embodiments, only one of all the X$^1$s and all the X$^2$s in each of the one or more units is

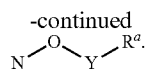

-continued

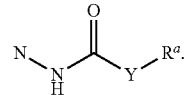

In some embodiments, at least one of all the X$^1$s and all the X$^2$s in the one or more units is

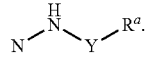

In some embodiments, at least one of all the X$^1$s and all the X$^2$s in the one or more units is

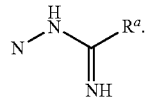

In some embodiments, at least one of all the X$^1$s and all the X$^2$s in the one or more units is

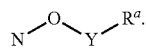

In some embodiments, at least one of all the X$^1$s and all the X$^2$s in the one or more units is

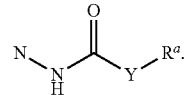

In some embodiments, R$^a$ is selected from the group consisting of OR$^1$, NR$^1$R$^2$, a primary, secondary, tertiary, or quaternary ammonium salt moiety, a pyridinium salt moiety, a guanidino or guanidinium salt moiety, a peptide, or an amino acid, wherein R$^1$ and R$^2$ are independently an H or a C1-C5 alkyl. Examples of ammonium salt moiety include —$^+$NR$_3$X$^-$, wherein R is a hydrogen or alkyl and X is a halide.

In some embodiments, Ar$^1$, Ar$^2$, Ar$^3$, and Ar$^4$ are each a phenyl group.

Another aspect of this patent document provides a medical device containing a surface coating comprising the polyarylene ether ketone polymer. While it is the surface coating or surface polymer that is being modified, the component(s) beneath the surface the medical device can remain untouched. Prior to any chemical modification, the surface polymer and the component(s) beneath can be the same or different. For example, a vertebral disk can be made from PEEK in its entirety.

In some embodiments, the device of this patent document is an orthopedic implant. Exemplary orthopedic devices or implants include screws, plates, rods, k-wires, pins, hooks, anchors, intramedullary devices, pedicle screws, pedicle hooks, spinal fusion cages, spinal fusion plates, prostheses, vertebrate disk implants, porous metal implants such as trabecular metal implants, and the like.

Other devices can have a metal core (e.g. titanium), which is coated with a polymer. Therefore, in a related aspect, this document provides a coating comprising the polyarylene ether ketone polymer. This coating on a medical device can, for example, promote osteoblast ingrowth.

Another aspect of this patent document provides a method of promoting spinal fusion, comprising implanting to a subject in need the medical device described herein. In an exemplary embodiment, a surgical procedure for stabilizing vertebrae in a spine includes the steps of:

Removing a damaged, degenerative, or defective bone structure (e.g. vertebral disk); and
Implanting a device described in this patent document (e.g. a surface modified PEEK vertebral disk);
wherein the implanted device promotes osteoblast ingrowth (e.g. promotes spinal fusion via osseointegration of new bone tissue into the device).

Another aspect of this patent document provides a method of modifying a medical device comprising a surface polymer comprising a plurality of repeating units, comprising
(a) contacting the surface polymer with an agent selected from the group consisting of

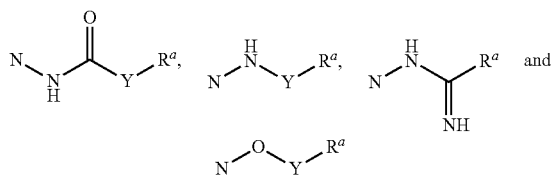

in a reaction medium,
wherein:
Y is a C1-C10 alkylene, wherein one or more carbons in the C1-C10 alkylene is optionally replaced with a heteroatom or a carbonyl; and
$R^a$ is selected from the group consisting of $OR^1$, $NR^1R^2$, C1-C5 alkyl, a primary, secondary, tertiary, or quaternary ammonium moiety, a pyridinium salt moiety, a guanidino or guanidinium salt moiety, a peptide, an amino acid, and zwitterionic species, wherein $R^1$ and $R^2$ are each an H or a C1-C5 alkyl; and
(b) allowing a ketone group of one or more units of the plurality of repeating units to react with the agent, whereby the ketone group of the one or more units is converted to a hydrophilic derivative group;
wherein the one or more units comprising the hydrophilic derivative group are independently represented by Formula I, Formula I

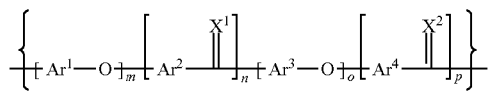

wherein:
$Ar^1$, $Ar^2$, $Ar^3$, and $Ar^4$ are each an optionally substituted aryl;
each of $X^1$ and $X^2$ is independently selected from O,

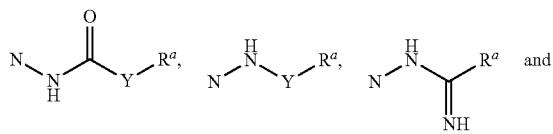

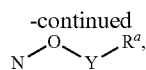

wherein:
Y is a C1-C10 alkylene, wherein one or more carbons in the C1-C10 alkylene is optionally replaced with a heteroatom, a carbonyl or $NR^1R^2$,
$R^a$ is selected from the group consisting of $OR^1$, $NR^1R^2$, C1-C5 alkyl, a primary, secondary, tertiary, or quaternary ammonium salt moiety, a pyridinium salt moiety, a guanidino or guanidinium salt moiety, a peptide, an amino acid, and zwitterionic species, wherein $R^1$ and $R^2$ are independently an H or a C1-C5 alkyl, and
provided that at least one of all the $X^1$s and all the $X^2$s in each of the one or more units is not O;
m and n are each an integer of 1, 2, or 3; and
and p are each an integer of 0, 1, or 2. The sub-embodiments of Formula I are as described above.

In some embodiments, a dip coating process may be used to react ketone moieties in the polymeric backbone with a suitable agent, as a means to improve the hydrophilicity of the polymer or the medical device. A dip coating process will have a distinct advantage over a spray coating process as a dip coat could react with all exposed surfaces of a device (e.g. an implant). Advantages of the present methods described herein include 1) mild reaction conditions—no solvent or temperatures that could impact the polymer's (e.g. PEEK) mechanical integrity, 2) a reaction product with a bond stable under physiological conditions, and 3) a reaction that has broad scope and availability to react with diverse substrates including small molecules, peptides, and growth factors.

For instance, the formation of an imine bond involves PEEK's ketone and a hydrophilic molecule bearing an aminooxy moiety (the reaction may also be extended to hydrazine moieties). The imine formation reaction does not require a catalyst, can be carried out in aqueous media or alcohols, and aminooxy groups can be introduced onto hydrophilic small molecules, peptides, and polymers.

Examples of agents containing a quarternary ammonium moiety or a pyridinium moiety include Girard reagents, which can be readily prepared or can be obtained from a commercial source. In some embodiments, the agent is not N-hydroxy amine ($NH_2OH$).

In some exemplary embodiments, the aminooxy hydrochloride salt is dissolved in a protic polar solvent (e.g. methanol or water), an aprotic polar solvent, or any mixture thereof and a polymer or device (e.g. disc) with a polyarylene ether polymer surface (e.g. PEEK) is added to the reaction media. In some embodiments, the reaction can proceed for about 2 hours, about 4 hours, about 8 hours, or about 24 hours, at a temperature of less than about 80° C., less than about 70° C., less than about 60° C., less than about 50° C., less than about 40° C., or less than about 30° C. Milder temperatures (i.e. room temperature) can be used as well. The modified polymer surface is characterized via contact angle measurements and X-ray photoelectron spectroscopy.

In some exemplary embodiments, the solvent can be chloroform, dichloromethane, tetrahydrofuran, N, N-dimethylformamide, acetone, alcohol, ethyl acetate, water, or any combination of these.

In some embodiments, the reaction medium has a pH of from about 2.0 to about 4.0, from about 1.5 to about 3.0, from about 2.0 to about 3.0. A buffer such as Glycine-HCl or Hydrochloric Acid-Potassium Chloride Buffer can be used to control the range of the pH of the reaction medium.

EXAMPLES

Example 1

Reaction of a PEEK film with Girard's Reagent D: A PEEK disk (0.26 mm thick, 200 mg) was washed with 95% methanol 5% water and added to a glass vial. The bis-HCl salt of Girard's reagent D (25 mg in 1 ml of 20:1 methanol/water) was added to the reaction vessel along with a magnetic stir bar. The vessel was sealed and the reaction was heated at 45° C. for 24 h. The disk was rinsed with methanol, ultra-pure water, and methanol.

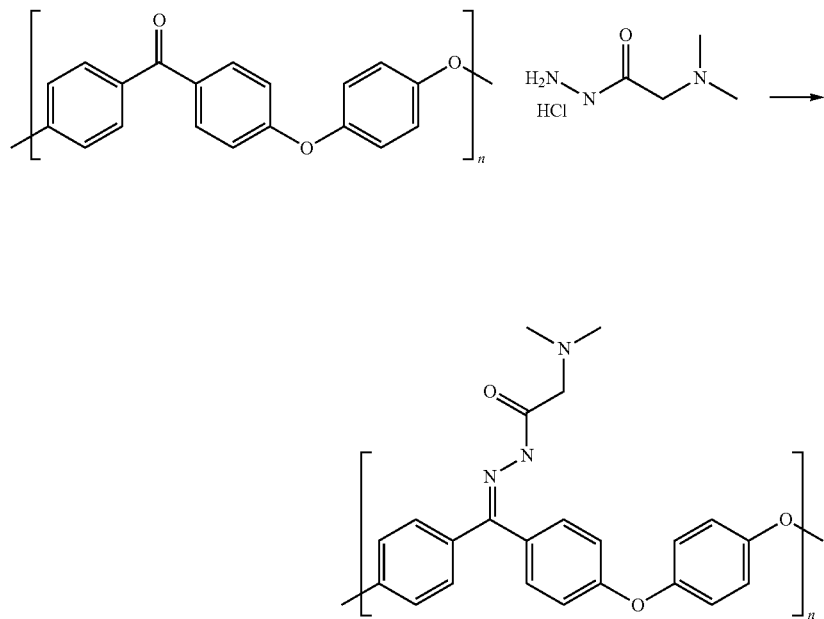

The reaction product was characterized using FT-IR and X-ray photoelectron spectroscopy (XPS). FT-IR spectroscopy revealed a new peak at 1050 cm$^{-1}$ due to the formation of surface modified PEEK. XPS was used to quantify the percent nitrogen on the PEEK surface as a means of proving the success of the reaction. XPS found the presence of 0.3% nitrogen on the PEEK surface. Ion etching the surface and measuring the XPS spectra showed 0% nitrogen detectable indicating that the introduced nitrogen is only on the PEEK surface. Water contact angle was determined to be 770 (plain PEEK film had a water contact angle of 90°).

Example 2

Reaction of a PEEK film with Girard's Reagent T: A PEEK disk (0.26 mm thick, 200 mg) was washed with 95% methanol 5% water and added to a glass vial. Girard's reagent T (25 mg in 1 ml of methanol) was added to the reaction vessel along with a magnetic stir bar. The mixture was then treated with 4 M HCl in dioxane (~80 µL) to form the corresponding hydrochloride salt of Girard's reagent T. The vessel was sealed and the reaction was heated at 45° C. for 24 h. The disk was rinsed with methanol, ultra-pure water, and methanol.

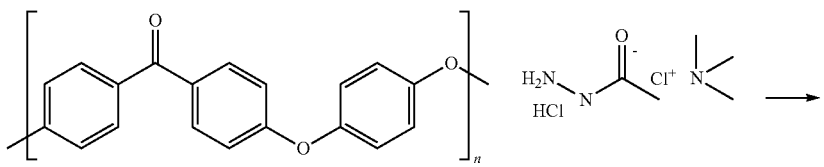

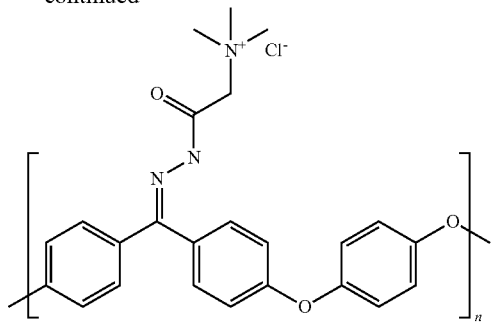

15

The reaction was characterized using FT-IR and X-ray photoelectron spectroscopy. FT-IR spectroscopy revealed a new peak at 1050 cm$^{-1}$ due to the formation of surface modified PEEK. XPS was used to quantify the percent nitrogen on the PEEK surface as a means of proving the success of the reaction. XPS found the presence of 1.1% nitrogen on the PEEK surface. Peaks in the XPS spectrum confirmed the presence of both hydrazine nitrogens and quaternary nitrogens. A water contact angle of 50° was obtained (plain PEEK film had a water contact angle of 90°).

Example 3

Reaction of a PEEK film with 2-(aminooxy)ethanamine: A PEEK disk (0.26 mm thick, 200 mg) was washed with 95% methanol 5% water and added to a glass vial. The bis-HCl salt of 2-(aminooxy)ethanamine (25 mg in 1 ml of 20:1 methanol/water) was added to the reaction vessel with a magnetic stir bar. The vessel was sealed and the reaction was heated at 45° C. for 24 h. The disk was rinsed with methanol, ultra-pure water, and methanol.

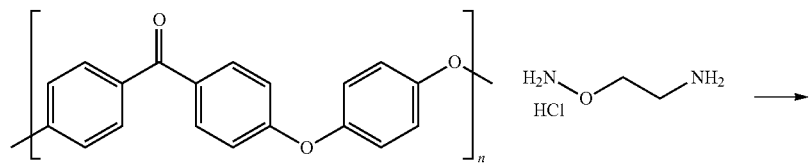

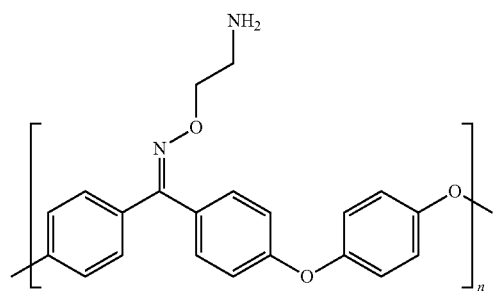

The reaction was characterized using FT-TR. FT-IR spectroscopy revealed a new peak at 1030 cm$^{-1}$ due to the formation of surface modified PEEK. XPS was used to quantify the percent nitrogen on the PEEK surface as a means of proving the success of the reaction. XPS found the presence of 1% nitrogen on the PEEK surface. A water contact angle of 77°. was obtained plain PEEK film had a water contact angle of 90°

Example 4

Reaction of a PEEK film with aminooxy-P15 peptide: A PEEK disk 0.26 mm thick (200 mg) was washed with 95% methanol 5% water and added to a glass vial. The trifluoroacetic acid salt of aminooxy-P15 (5 mg in 0.5 mL of ultra-pure Millipore H$_2$O) was added to the reaction vessel with a magnetic stir bar. The reaction was heated at 45° C. for 24 h. The disk was rinsed with methanol, ultra-pure water, and methanol.

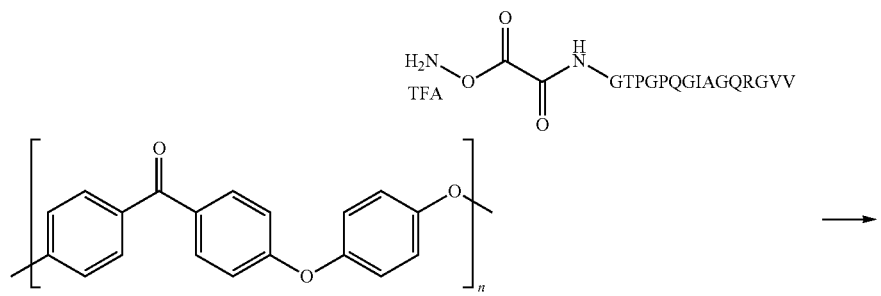

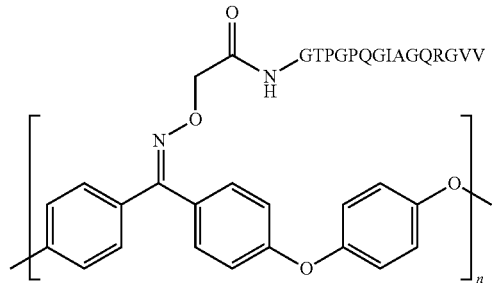

The reaction was characterized using XPS to quantify the percent nitrogen on the PEEK surface as a means of proving the success of the reaction. XPS found the presence of 3% nitrogen on the PEEK surface. Ar+ ion etching of the P15-reacted surface removed the nitrogen signal demonstrating that the peptide was located only at the surface of the treated PEEK.

Example 5

Reaction of a PEEK film with aminoguanidine hydrochloride: A PEEK disc 0.3 mm thick (200 mg) was washed with 95% methanol and 5% water and added to a glass vial. The vial was charged with a magnetic stir bar and the disc was then treated with a solution of aminoguanidine HCl in ultrapure H$_2$O (200 mg in 2 mL or 100 mg/mL). The vial was sealed and heated at 45° C. for 24 h. The disc was removed from the heat and cooled to ambient temperature. After cooling, the disc was washed with ultrapure H$_2$O and 70% EtOH then placed in a 6 well plate to dry.

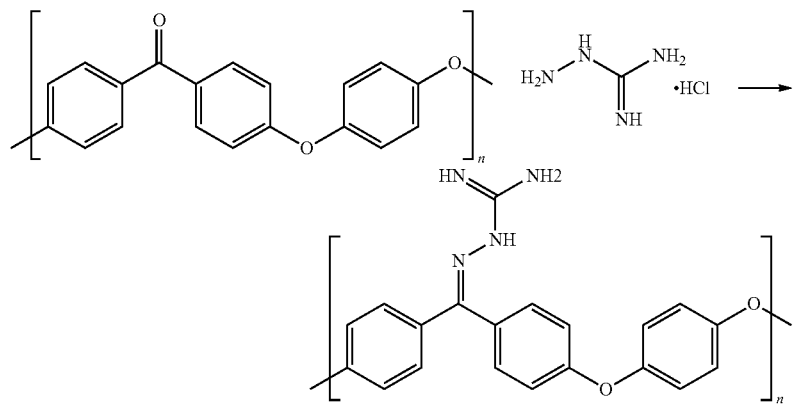

Example 6

Static water contact angles (θ) for PEEK films produced in Examples 1-4 above were measured to verify surface modification and estimate hydrophilicity (Table 1). Measurements were obtained using a VCA Optima contact angle instrument (AST Products, Inc.) with a drop size of 1.0 μL of deionized water. Unmodified PEEK displayed a contact angle of 91° indicative of its hydrophobic nature. Samples with θ>91° were viewed as being more hydrophobic than PEEK, while samples with θ<91° were viewed as being more hydrophilic. PEEK surfaces modified with oxyamine or hydrazine nucleophiles in examples 1, 2, and 3 possessed a greater degree of hydrophilicity relative to unmodified PEEK with contact angles of 77, 51°, and 80° respectively. The product of example 4, which was derived from P15-peptide, exhibited a contact angle very comparable to PEEK itself (θ=92°).

Example 7

X-ray photoelectron spectroscopy (XPS), was used to provide further evidence of the success of the surface modification reactions. XPS was conducted via a Thermo Fisher ESCALAB 250 Xi spectrometer with an Al Kα source and a 0.9 mm spot size with charge compensation. Spectra were taken and recorded under normal emission conditions for the work products from examples 1-4 above and an unmodified PEEK surface (take-off angle of 90° from the plane of the surface). Nis region spectra for the samples are shown in FIG. 1. Each modified sample exhibited a characteristic Nis binding energy peak in the XPS spectrum at 399 eV corresponding to the oxyamine or hydrazine nitrogen atoms bound to the polymer surface. The modified PEEK surfaces prepared with Girard's reagent T (Example 2) displayed an additional peak at 402 eV confirming the presence of the quaternary alkyl ammonium nitrogen.

Additional evidence of the surface modification was obtained via Ar+ ion etching experiments. Ion etching of the polymer surface at 20 sec intervals and subsequent analysis via XPS showed a continual decrease in the nitrogen binding energy peak in the Nis region spectra for peptide-modified PEEK example 4, indicating that the introduced nitrogen was only present on the PEEK surface.

It will be appreciated by persons skilled in the art that the present invention is not limited to what has been particularly shown and described. Rather, the scope of the present invention is defined by the claims which follow. It should further be understood that the above description is only representative of illustrative examples of embodiments. The description has not attempted to exhaustively enumerate all possible variations. The alternate embodiments may not have been presented for a specific portion of the invention, and may result from a different combination of described portions, or that other un-described alternate embodiments may be available for a portion, is not to be considered a disclaimer of those alternate embodiments. It will be appreciated that many of those un-described embodiments are within the literal scope of the following claims, and others are equivalent.

The invention claimed is:

1. A polyarylene ether ketone polymer having a plurality of repeating units, wherein a ketone group in one or more units of the plurality of repeating units comprises a hydrophilic N-substituted imine, wherein the one or more units comprising the hydrophilic N-substituted imine are independently represented by Formula I, Formula I

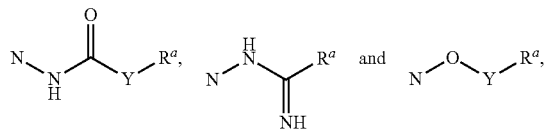

wherein:
Ar$^1$, Ar$^2$, Ar$^3$, and Ar$^4$ are each an optionally substituted aryl;
each of X$^1$ and X$^2$ is independently selected from the group consisting of O,

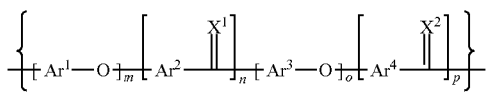

wherein:
Y is a C1-C10 alkylene, wherein one or more carbons in the C1-C10 alkylene are independently and optionally replaced with a heteroatom, a carbonyl, or NR$^1$R$^2$,
R$^a$ is selected from the group consisting of OR$^1$, NR$^1$R$^2$, C1-C5 alkyl, a primary, secondary, tertiary, or quaternary ammonium salt moiety, a pyridinium salt moiety, a guanidino or guanidinium salt moiety, a peptide, an amino acid, and a zwitterionic species, wherein R$^1$ and R$^2$ are independently an H or a C1-C5 alkyl, and
provided that at least one of all the X$^1$s and all the X$^2$s in each of the one or more units is not O;
m and n are each an integer of 1, 2, or 3; and
o and p are each an integer of 0, 1, or 2.

2. The polyarylene ether ketone polymer of claim 1, wherein the one or more units account for about 0.1% to about 25% of the plurality of repeating units.

3. The polyarylene ether ketone polymer of claim 1, wherein the one or more units account for about 0.1% to about 10% of the plurality of repeating units.

4. The polyarylene ether ketone polymer of claim 1, wherein o and p are each 0.

5. The polyarylene ether ketone polymer of claim 1, wherein m is 1, n is 1, and o and p are each 0.

6. The polyarylene ether ketone polymer of claim 1, wherein m is 1, n is 1, o is 0, and p is 1.

7. The polyarylene ether ketone polymer of claim 1, wherein only one of all the X$^1$s and all the X$^2$s in each of the one or more units is selected from the group consisting of

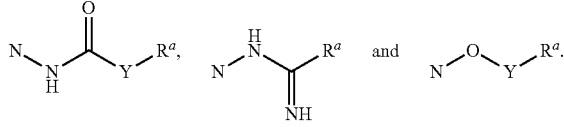

8. The polyarylene ether ketone polymer of claim 1, wherein at least one of all the X$^1$s and all the X$^2$s in the one or more units is

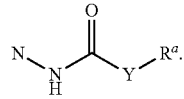

9. The polyarylene ether ketone polymer of claim 1, wherein at least one of all the X$^1$s and all the X$^2$s in the one or more units is

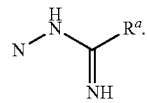

10. The polyarylene ether ketone polymer of claim 1, wherein at least one of all the X$^1$s and all the X$^2$s in the one or more units is

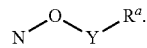

11. The polyarylene ether ketone polymer of claim 1, wherein R$^a$ is selected from the group consisting of OR$^1$, NR$^1$R$^2$, a quaternary ammonium salt moiety, a pyridinium salt moiety, a guanidino salt moiety, a guanidinium salt moiety, and a peptide.

12. The polyarylene ether ketone polymer of claim 1, wherein Ar$^1$, Ar$^2$, Ar$^3$, and Ar$^4$ are each a phenyl group.

13. A medical device comprising a surface coating comprising a polyarylene ether ketone polymer having a plurality of repeating units, wherein a ketone group in one or more units of the plurality of repeating units comprises a hydrophilic N-substituted imine, wherein the device is an implant, wherein the one or more units comprising the hydrophilic N-substituted imine are independently represented by Formula I, Formula I

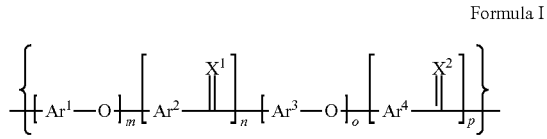

wherein:
Ar$^1$, Ar$^2$, Ar$^3$, and Ar$^4$ are each an optionally substituted aryl;
each of X$^1$ and X$^2$ is independently selected from the group consisting of O,

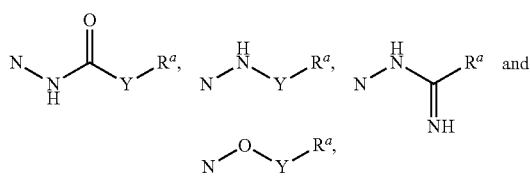

wherein:
Y is a C1-C10 alkylene, wherein one or more carbons in the C1-C10 alkylene are independently and optionally replaced with a heteroatom, a carbonyl, or $NR^1R^2$, $R^a$ is selected from the group consisting of $OR^1$, $NR^1R^2$, C1-C5 alkyl, a primary, secondary, tertiary, or quaternary ammonium salt moiety, a pyridinium salt moiety, a guanidino or guanidinium salt moiety, a peptide, an amino acid, and a zwitterionic species, wherein $R^1$ and $R^2$ are independently an H or a C1-C5 alkyl, and provided that at least one of all the $X^1$s and all the $X^2$s in each of the one or more units is not O;

m and n are each an integer of 1, 2, or 3; and o and p are each an integer of 0, 1, or 2.

14. The medical device of claim 13, which is an orthopedic implant.

15. The medical device of claim 13, wherein the one or more units account for about 0.1% to about 25% of the plurality of repeating units.

16. The medical device of claim 13, wherein the one or more units account for about 0.1% to about 10% of the plurality of repeating units.

17. The medical device of claim 13, wherein at least one of all the $X^1$s and all the $X^2$s in the one or more units is

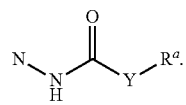

18. The medical device of claim 13, wherein at least one of all the $X^1$s and all the $X^2$s in the one or more units is

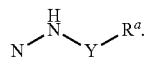

19. The medical device of claim 13, wherein at least one of all the $X^1$s and all the $X^2$s in the one or more units is

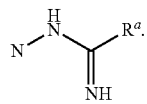

20. The medical device of claim 13, wherein at least one of all the $X^1$s and all the $X^2$s in the one or more units is

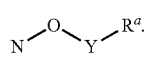

21. The medical device of claim 13, wherein $R^a$ is selected from the group consisting of $OR^1$, $NR^1R^2$, a quaternary ammonium salt moiety, a pyridinium salt moiety, a guanidino salt moiety, a guanidinium salt moiety, and a peptide.

22. The medical device of claim 13, wherein $Ar^1$, $Ar^2$, $Ar^3$, and $Ar^4$ are each a phenyl group.

23. The medical device of claim 13, wherein $R^a$ is $OR^1$ or $NR^1R^2$.

24. The medical device of claim 13, wherein o and p are each 0.

25. The medical device of claim 13, wherein m is 1, n is 1, and o and p are each 0.

26. The medical device of claim 13, wherein m is 1, n is 1, o is 0, and p is 1.

27. A medical device comprising a surface coating comprising a polyarylene ether ketone polymer having a plurality of repeating units, wherein a ketone group in one or more units of the plurality of repeating units comprises a hydrophilic N-substituted imine, wherein the one or more units comprising the hydrophilic N-substituted imine are independently represented by Formula I, Formula I

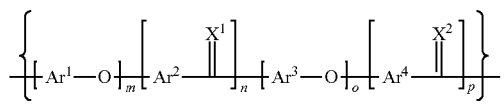

wherein:
$Ar^1$, $Ar^2$, $Ar^3$, and $Ar^4$ are each an optionally substituted aryl;

each of $X^1$ and $X^2$ is independently selected from the group consisting of O,

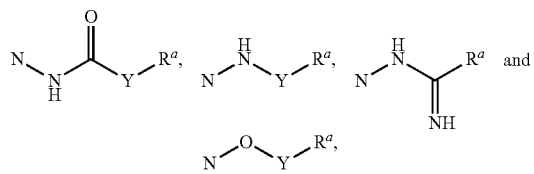

wherein:
Y is a C1-C10 alkylene, wherein one or more carbons in the C1-C10 alkylene are independently and optionally replaced with a heteroatom, a carbonyl, or $NR^1R^2$, $R^a$ is selected from the group consisting of $OR^1$, $NR^1R^2$, C1-C5 alkyl, a primary, secondary, tertiary, or quaternary ammonium salt moiety, a pyridinium salt moiety, a guanidino or guanidinium salt moiety, a peptide, an amino acid, and a zwitterionic species, wherein $R^1$ and $R^2$ are independently an H or a C1-C5 alkyl, and provided that at least one of all the $X^1$s and all the $X^2$s in each of the one or more units is not O;

m and n are each an integer of 1, 2, or 3; and o and p are each an integer of 0, 1, or 2.

28. A method of promoting spinal fusion, comprising implanting to a subject in need the medical device of claim 13.

29. The method of claim 28, which promotes osseointegration of new bone tissue into the medical device.

30. A method of modifying a medical device comprising a surface polymer comprising a plurality of repeating units, comprising
  (a) contacting the surface polymer with an agent selected from the group consisting of

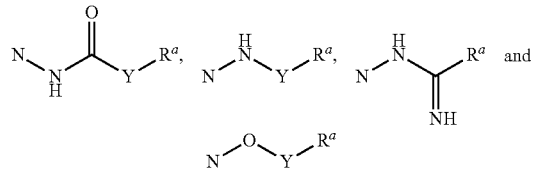

in a reaction medium
wherein:
Y is a C1-C10 alkylene, wherein one or more carbons in the C1-C10 alkylene is optionally replaced with a heteroatom or a carbonyl; and
$R^a$ is selected from the group consisting of $OR^1$, $NR^1R^2$, C1-C5 alkyl, a primary, secondary, tertiary, or quaternary ammonium moiety, a pyridinium salt moiety, a guanidino or guanidinium salt moiety, a peptide, an amino acid, and a zwitterionic species, wherein $R^1$ and $R^2$ are each an H or a C1-C5 alkyl; and
  (b) allowing a ketone group of one or more units of the plurality of repeating units to react with the agent, whereby the ketone group of the one or more units is converted to a hydrophilic derivative group;
wherein each of the plurality of repeating units in the hydrophilic derivative group is independently represented by Formula I, Formula I

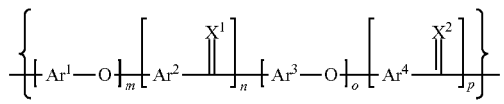

wherein:
$Ar^1$, $Ar^2$, $Ar^3$, and $Ar^4$ are each an optionally substituted aryl;
each of $X^1$ and $X^2$ is independently selected from O,

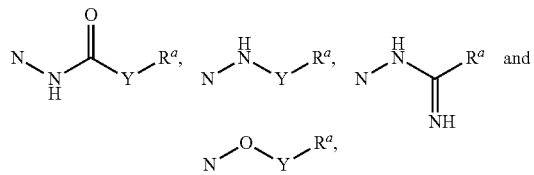

wherein:
Y is a C1-C10 alkylene, wherein one or more carbons in the C1-C10 alkylene is optionally replaced with a heteroatom, a carbonyl or $NR^1R^2$,
$R^a$ is selected from the group consisting of $OR^1$, $NR^1R^2$, C1-C5 alkyl, a primary, secondary, tertiary, or quaternary ammonium salt moiety, a pyridinium salt moiety, a guanidino or guanidinium salt moiety, a peptide, an amino acid, or a zwitterionic species, wherein $R^1$ and $R^2$ are independently an H or a C1-C5 alkyl, and
provided that at least one of all the $X^1$s and all the $X^2$s in each of the one or more units is not O;
m and n are each an integer of 1, 2, or 3; and
o and p are each an integer of 0, 1, or 2.

31. The method of claim 30, wherein the molar ratio between the surface polymer and the agent ranges from about 10:1 to about 1:100.

32. The method of claim 30, wherein the reaction medium has a pH ranging from about 1.5 to about 3.

33. The method of claim 30, wherein the reaction medium has a pH about 2.0.

34. The method of claim 30, wherein the reaction medium comprises an acid, and the acid and the surface polymer are in a molar ratio ranging from about 100:1 to about 1:100.

35. The method of claim 30, wherein the agent is in a form of an acid salt.

36. The method of claim 30, wherein the agent is in a concentration ranging from about 0.1 mg/ml to about 1000 mg/ml.

37. The method of claim 30, wherein the agent is in a concentration ranging from about 0.1 mg/ml to about 50 mg/ml.

38. The method of claim 30, wherein the surface polymer is submerged in the reaction medium.

39. The method of claim 30, wherein the reaction medium comprises a polar solvent.

40. The method of claim 30, wherein step (b) takes place at a temperature of less than about 65° C.

41. The method of claim 30, wherein the medical device is an implant.

* * * * *